US012606513B2

(12) United States Patent
Hirano et al.

(10) Patent No.: US 12,606,513 B2
(45) **Date of Patent: *Apr. 21, 2026**

(54) FORMATE PRODUCTION METHOD, FORMIC ACID PRODUCTION METHOD, AND ANTIFREEZING AGENT PRODUCTION METHOD

(71) Applicant: NITTO DENKO CORPORATION, Ibaraki (JP)

(72) Inventors: Makoto Hirano, Ibaraki (JP); Hirokazu Matsuda, Ibaraki (JP); Evgeny Alexandrovich Pidko, Utrecht (NL); Georgy Alexandrovich Filonenko, Delft (NL); Christophe Rebreyend, Delft (NL)

(73) Assignee: NITTO DENKO CORPORATION, Ibaraki (JP)

( * ) Notice: Subject to any disclaimer, the term of this patent is extended or adjusted under 35 U.S.C. 154(b) by 453 days.

This patent is subject to a terminal disclaimer.

(21) Appl. No.: 18/043,973

(22) PCT Filed: Aug. 30, 2021

(86) PCT No.: PCT/JP2021/031792

§ 371 (c)(1),
(2) Date: Mar. 3, 2023

(87) PCT Pub. No.: WO2022/050235

PCT Pub. Date: Mar. 10, 2022

(65) Prior Publication Data

US 2023/0312448 A1 Oct. 5, 2023

(30) Foreign Application Priority Data

Sep. 3, 2020 (JP) ................................ 2020-148562
Feb. 12, 2021 (JP) ................................ 2021-021223
(Continued)

(51) Int. Cl.
*C07C 51/02* (2006.01)
*B01J 31/16* (2006.01)
(Continued)

(52) U.S. Cl.
CPC ........... *C07C 51/02* (2013.01); *B01J 31/1616* (2013.01); *B01J 31/181* (2013.01); *B01J 31/189* (2013.01);
(Continued)

(58) Field of Classification Search
CPC ......... C07C 51/02; C07C 51/41; C07C 53/02; C07C 53/06
See application file for complete search history.

(56) References Cited

U.S. PATENT DOCUMENTS 10,300,469 B1 * 5/2019 Huang ...................... C01B 3/22
2015/0166337 A1 6/2015 Himeda et al.

FOREIGN PATENT DOCUMENTS

CA 1338802 C * 12/1996 ........... C07C 209/68
CN 104193611 A 12/2014
(Continued)

OTHER PUBLICATIONS

Filonenko, G., et al., Highly efficient reversible hydrogenation of carbon dioxide to formates using a ruthenium PNP-Pincer catalyst, Chemcatchem communications, vol. 6, No. 6, pp. 1526-1530 (Year: 2014).*

(Continued)

*Primary Examiner* — Yate' K Cutliff
(74) *Attorney, Agent, or Firm* — Hauptman Ham, LLP

(57) ABSTRACT

The invention relates to a method for producing a formate, the method including a first step of reacting hydrogen with carbon dioxide, a hydrogen carbonate or a carbonate using a catalyst in the presence of a solvent to form a formate in the reaction liquid, wherein the reaction is a two-phase
(Continued)

system in which an organic phase and an aqueous phase are present in a separated state in the solvent, and a base concentration in the reaction is 2.5 mol/L or more.

11 Claims, 2 Drawing Sheets

(30) Foreign Application Priority Data

| | | | |
|---|---|---|---|
| Feb. 12, 2021 | (JP) | ................................ | 2021-021224 |
| Feb. 12, 2021 | (JP) | ................................ | 2021-021225 |
| May 10, 2021 | (JP) | ................................ | 2021-079887 |
| May 17, 2021 | (JP) | ................................ | 2021-083416 |

(51) Int. Cl.

| | |
|---|---|
| ***B01J 31/18*** | (2006.01) |
| ***B01J 31/20*** | (2006.01) |
| ***B01J 31/24*** | (2006.01) |
| ***C07C 51/41*** | (2006.01) |
| ***C07F 15/00*** | (2006.01) |
| ***C09K 3/18*** | (2006.01) |
| *C07C 51/15* | (2006.01) |

(52) U.S. Cl.

CPC ........... *B01J 31/20* (2013.01); *B01J 31/2409* (2013.01); *C07C 51/41* (2013.01); *C07F 15/0046* (2013.01); *C09K 3/185* (2013.01); *B01J 2231/648* (2013.01); *B01J 2531/004* (2013.01); *B01J 2531/821* (2013.01); *C07C 51/15* (2013.01)

(56) References Cited

FOREIGN PATENT DOCUMENTS

| | | | | |
|---|---|---|---|---|
| CN | 104418530 | | * | 3/2015 |
| CN | 104418530 | A | | 3/2015 |
| CN | 105949631 | A | | 9/2016 |
| CN | 106083559 | A | | 11/2016 |
| EP | 0 357 243 | A2 | | 3/1990 |
| JP | H2-91038 | A | | 3/1990 |
| JP | H7-299333 | A | | 11/1995 |
| JP | H10-36310 | | * | 2/1998 |
| JP | H10-36310 | A | | 2/1998 |
| JP | 2003-135620 | A | | 5/2003 |
| JP | 2007-55915 | A | | 3/2007 |
| JP | 5367190 | B1 | | 12/2013 |
| JP | 2015-505857 | A | | 2/2015 |
| JP | 5896539 | B2 | | 3/2016 |
| JP | 2016-539793 | A | | 12/2016 |
| WO | 2015/083007 | A1 | | 6/2015 |

OTHER PUBLICATIONS

Kakkie et al., Synthesis and reactivity of Zr MOFs assembled form PNNN P—Ru Pincer complexes, organometallics, vol. 38, No. 18. pp. 3419 - 3428 (Year 2019) (Year: 2019).*

Office Action dated Jan. 14, 2025 for corresponding Japanese Patent Application No. 2022-546318, along with an English translation (7 pages).

Ryo Tanaka et al., "Catalytic Hydrogenation of Carbon Dioxide Using Ir(III)-Pincer Complexes", Journal of the American Chemical Society, vol. 131, No. 40, Sep. 23, 2009, pp. 14168-14169, cited in NPL No. 1.

Federica Bertini et al., "Efficient and Mild Carbon Dioxide Hydrogenation to Formate Catalyzed by Fe(II) Hydrido Carbonyl Complexes Bearing 2,6-(Diaminopyridyl)diphosphine Pincer Ligands", ACS Catalysis, vol. 6(5), Mar. 30, 2016, pp. 2889-2893, cited in NPL No. 1.

The Extended European Search Report issued on Oct. 2, 2024 for corresponding European Patent Application No. 21864293.2 (11 pages).

Filonenko et al., "Highly Efficient Reversible Hydrogenation of Carbon Dioxide to Formates Using a Ruthenium PNP-Pincer Catalyst", ChemCatChem, vol. 6, No. 6, Apr. 17, 2014, pp. 1526-1530 (5 pages), cited in NPL No. 1.

Konrath et al., "Preparation of a Series of Supported Nonsymmetrical PNP-Pincer Ligands and the Application in Ester Hydrogenation", Chemistry A European Journal, vol. 25, Nov. 4, 2019, pp. 15341-15350 (10 pages), cited in NPL No. 1.

Arenas et al., "Synthesis of a p. Stereogenic PNPtBu, Ph Ruthenium Pincer Complex and Its Application in Asymmetric Reduction of Ketones", European Journal of Organic Chemistry, vol. 2015, No. 17, May 8, 2015, pp. 3666-3669 (4 pages), cited in NPL No. 1.

Kassie et al., "Synthesis and Reactivity of Zr MOFs Assembled from PNNNP-Ru Pincer Complexes", Organometallics, vol. 38, No. 18, Sep. 6, 2019, pp. 3419-3428 (10 pages), cited in NPL No. 1.

Gunasekar et al., "Eco-friendly upconversion of limestone into value-added calcium formate", Green Chemistry, vol. 22, No. 15, Jun. 29, 2020, pp. 4995-5001 (7 pages), cited in NPL No. 1.

Joszai et al., "Hydrogenation of aqueous mixtures of calcium carbonate and carbon dioxide using a water-soluble rhodium(I)-tertiary phosphine complex catalyst", Journal of Molecular Catalysis A: Chemical, vol. 224, No. 1-2, Dec. 15, 2004, pp. 87-91 (5 pages), cited in NPL No. 1.

Notice of Reasons for Refusal, dated Feb. 4, 2025, for the corresponding Japanese Patent Application No. 2022-546316, along with English machine translation (10 pages).

Notice of Reasons for Refusal, dated Mar. 5, 2025, for the corresponding Japanese Patent Application No. 2022-546317, along with English machine translation (5 pages).

David Benito-Garagorri et al., "Achiral and Chiral Transition Metal Complexes with Modularly Designed Tridentate PNP Pincer-Type Ligands Based on N-Heterocyclic Diamines", Organometallics, Mar. 15, 2006, vol. 25, No. 8, pp. 1900-1913, Cited in NPL No. 1. (15 pages).

Kentaro Matayoshi et al., "Synthesis and Crystal Structure of [RuCl3{N, N'-bis(diphenylphosphino)-2,6-diaminopyridine}]·3CH3OH", X-ray Structure Analysis Online, 2012, vol. 28, pp. 57-58, Cited in NPL No. 1. (3 pages).

Office Action issued on Apr. 8, 2025 for corresponding Chinese Patent Application No. 202180054363.1, along with English machine translation (19 pages).

International Search Report issued for corresponding International Patent Application No. PCT/JP2021/031792 on Oct. 26, 2021, along with an English translation (5 pages). 2021 (3 pages).

Written Opinion issued for corresponding International Patent Application No. PCT/JP2021/031792 on Oct. 26,.

Hameed et al., "Visible-Light Photocatalytic Reduction of $CO_2$ to Formic Acid with a Ru Catalyst Supported by N, N'-Bis (diphenylphosphino)-2,6-diaminopyridine Ligands", CHEMSUSCHEM Communications 2019, vol. 12, No. 15, pp. 3453-3457 (5 pages), cited in NPL Nos. 1 and 2.

Alvarez et al., "Challenges in the Greener Production of Formates/Formic Acid, Methanol, and DME by Heterogeneously Catalyzed CO2 Hydrogenation Processes", Chemical Reviews, 2017, 117, 14, pp. 9804-9838 (35 pages), cited in the Specification.

Sordakis et al., "Homogeneous Catalysis for Sustainable Hydrogen Storage in Formic Acid and Alcohols", Chemical Reviews, 2018, 118, 2, pp. 372-433 (62 pages), cited in the Specification.

Office Action dated Jun. 3, 2025, for corresponding Japanese Patent Application No. 2022-546317, along with an English translation (7 pages).

Office Action issued for corresponding Indonesian Patent Application No. P00202301924 on Jul. 1, 2025, along with an English translation (8 pages).

* cited by examiner

FORMATE PRODUCTION METHOD, FORMIC ACID PRODUCTION METHOD, AND ANTIFREEZING AGENT PRODUCTION METHOD

CROSS REFERENCE TO RELATED APPLICATION

This application is a National Stage of International Application No. PCT/JP2021/031792, filed on Aug. 30, 2021, which designates the United States and was published in Japan, and which is based upon and claims priority to Japanese Patent Application Nos.: 1) 2020-148562, filed on Sep. 3, 2020; 2) 2021-021223, filed on Feb. 12, 2021; 3) 2021-021224, filed on Feb. 12, 2021; 4) 2021-021225, filed on Feb. 12, 2021; 5) 2021-079887, filed on May 10, 2021; and 6) 2021-083416, filed on May 17, 2021 in the Japan Patent Office. All of the aforementioned applications are hereby incorporated by reference in their entireties.

TECHNICAL FIELD

The present invention relates to a method for producing a formate, a method for producing formic acid, and a method for producing an antifreezing agent.

BACKGROUND ART

As solution means for the problems of global warming and depletion of fossil fuel, high expectations are placed on a technology for converting carbon dioxide into a useful compound and hydrogen energy as a next-generation energy.

Formic acid is such that energy necessary for a dehydrogenation reaction is low and simple handing is possible, and therefore, formic acid is considered as an excellent compound as a hydrogen storage material. Thus, attention has been paid to technologies for converting a formate to formic acid and technologies for converting carbon dioxide to formic acid.

For example, Patent Literatures 1 and 2 describe methods for efficiently separating and recovering an organic acid from a mixed solution of the organic acid and a metal salt thereof by electrodialysis methods, and a method for producing formic acid from a formate is investigated.

Furthermore, a method for producing lithium hydroxide by subjecting mineral acid lithium to electrodialysis, the method being capable of stably producing lithium hydroxide by preliminarily adding an organic acid to decarbonate, is investigated in Patent Literature 3.

CITATION LIST

Patent Literature

Patent Literature 1: JPH07-299333A
Patent Literature 2: JPH10-36310A
Patent Literature 3: JP5367190B

SUMMARY OF INVENTION

Technical Problem

Further improvement is necessary for the yield of the production of formic acid in the related art technologies, and the development of a method that can form formic acid in higher yield and with excellent productivity is required.

Thus, the invention provides a method for producing a formate, in which a formate as a precursor of formic acid can be produced in high yield and with excellent productivity, a method for producing formic acid, and a method for producing an antifreezing agent.

Solution to Problem

As a result of intensive investigations, the present inventors have found a method for producing a formate, in which the formate can be produced in high yield and with excellent productivity, and have completed the invention.

Means for solving the above problems are as follows.

<1> A method for producing a formate, the method comprising:

a first step of reacting hydrogen with carbon dioxide, a hydrogen carbonate or a carbonate using a catalyst in the presence of a solvent to form the formate in a reaction liquid, wherein the reaction is a two-phase system in which an organic solvent and an aqueous solvent are present in a separated state in the solvent, and the base concentration in the reaction is 2.5 mol/L or more.

<2> The method for producing a formate described in <1>, wherein the catalyst has a catalyst turnover number: TON, which can be determined by the following calculation method, of 10000 or more:

TON calculation method:

$$TON = X/Y \quad \text{formula 1}$$

(in the formula 1, X represents a molar amount X (mol) of potassium formate formed by the following TON calculation reaction, a value of X is calculated by the following formula 2, and Y represents a molar amount (mol) of the catalyst used for the following reaction.)

$$X = (W/M) \times (Ia \times Ib/R) \times (A/B) \quad \text{formula 2}$$

(in the formula 2, W represents an amount (g) of dimethyl sulfoxide used for quantification of potassium formate, M represents a molecular weight of dimethyl sulfoxide, R represents a ratio of the number of protons of dimethyl sulfoxide to the number of protons of potassium formate, Ia represents a proton NMR integration value of potassium formate, Ib represents a proton NMR Integration value of dimethyl sulfoxide, A represents a mass (g) of an aqueous solution in a lower layer obtained by the following reaction, and B represents a mass (g) of an aqueous solution used for quantification of potassium formate.)

TON calculation reaction:

(Production of formate)

10 mmol of $KHCO_3$ was added to 1 mL of water in a glass vial equipped with a stirring rod in a glovebox under an inert gas, subsequently 0.12 μmol of a catalyst and 54 μmol of methyltrioctylammonium chloride were added to 1 mL of a solvent in which the catalyst obtains the highest TON and which is selected from toluene, dioxane, tetrahydrofuran, ethyl acetate, methylcyclohexane, and cyclopentyl methyl ether, thereafter the vial was placed in an autoclave, the autoclave was sealed and taken out of the glovebox, the autoclave was heated to 90° C. while being stirred, when the temperature reached the target temperature, the autoclave was pressurized to 4.5 MPa with $H_2$, the reaction mixture was stirred for 18 hours, thereafter the reaction mixture was cooled with an ice bath, pressure was released, and an upper layer of the solution after the reaction was removed, and A g of an aqueous solution of a lower layer containing potassium formate and unreacted $KHCO_3$ was obtained;

(Quantification of Potassium Formate)

B g of the aqueous solution of the lower layer was collected and dissolved in 500 μL of deuterated water, W g of dimethyl sulfoxide was added as an internal standard, thereafter $^1H$ NMR analysis was performed, and an NMR integration value of potassium formate was designated as Ia, while an NMR integration value of dimethyl sulfoxide was designated as Ib.

<3> The method for producing a formate described in <1> or <2>, wherein the catalyst is a metal complex catalyst, and a ligand of the metal complex catalyst is further added.

<4> The method for producing a formate described in <1> or <2>, wherein the catalyst is at least one selected from a ruthenium complex represented by the following formula (1), a tautomer or stereoisomer thereof, and a salt compound of the complex, tautomer or stereoisomer:

[Chem. 1]

(1)

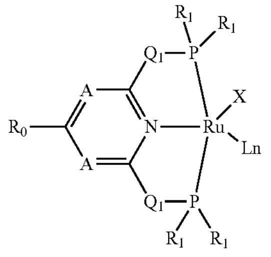

(in the formula (1), $R_0$ represents a hydrogen atom or an alkyl group, $Q_1$ each independently represents $CH_2$, NH or O, $R_1$ each independently represents an alkyl group or an aryl group (provided that when $Q_1$ represents NH or O, at least one of $R_1$ represents an aryl group), A each independently represents CH, $CR_5$ or N, $R_5$ represents an alkyl group, an aryl group, an aralkyl group, an amino group, a hydroxy group or an alkoxy group, X represents a halogen atom, n represents 0 to 3, and when more than one L are present, L each independently represents a neutral or anionic ligand.)

<5> The method for producing a formate described in <4>, wherein a ligand represented by the following formula (4) is further added:

[Chem. 2]

(4)

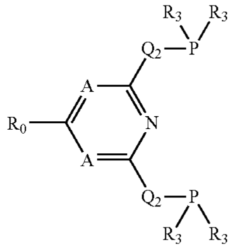

(In the formula (4), $R_0$ represents a hydrogen atom or an alkyl group, $Q_2$ each independently represents NH or O, $R_3$ each independently represents an aryl group, A each independently represents CH, $CR_5$ or N, and $R_5$ represents an alkyl group, an aryl group, an aralkyl group, an amino group, a hydroxy group or an alkoxy group.)

<6> The method for producing a formate described in any one of <1> to <5>, wherein the organic phase contains toluene or dioxane.

<7> The method for producing a formate described in any one of <1> to <6>, wherein in the first step, a quaternary ammonium salt is used as a phase transfer catalyst.

<8> A method for producing formic acid, the method comprising:

a step of producing a formate by the method described in any one of <1> to <7>; and a second step of protonating at least a part of the formate by electrodialysis to form formic acid and water.

<9> The method for producing formic acid described in <8>, wherein the aqueous phase is separated, a concentration of the formate in the aqueous phase is adjusted by dilution, and then the aqueous phase is used in the second step.

<10> The method for producing formic acid described in <9>, wherein the water formed in the second step is used for the dilution.

<11> The method for producing formic acid described in <8>, wherein the aqueous phase is separated, an acid is added thereto to conduct a decarbonation treatment, and then the aqueous phase is used in the second step.

<12> A method for producing an antifreezing agent, the method comprising:

a step of producing a formate by the method for producing a formate described in any one of <1> to <7>.

<13> The method for producing an antifreezing agent described in <12>, wherein the method further includes a step of adding at least one or more acids selected from the group consisting of formic acid and acetic acid to the formate.

Advantageous Effects of Invention

According to the invention, a method for producing a formate, in which a formate can be produced in high yield and with excellent productivity, a method for producing formic acid, and a method for producing an antifreezing agent can be provided.

DESCRIPTION OF EMBODIMENTS

Figure 1:
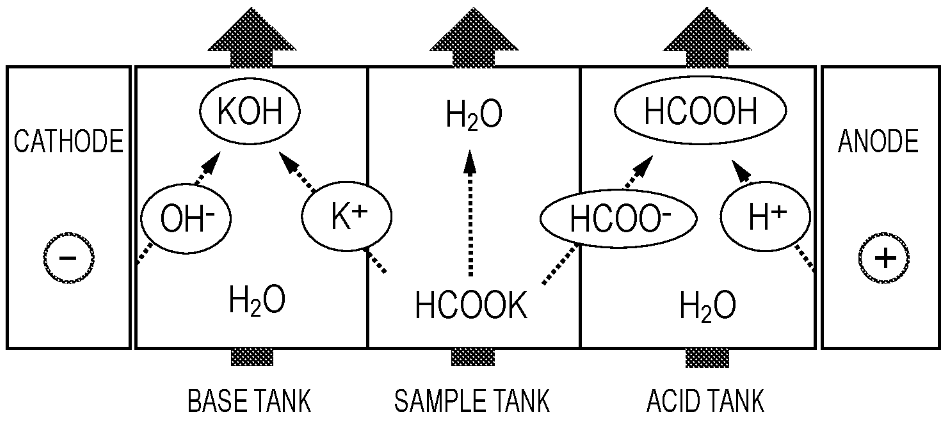
FIG. 1 is a schematic diagram illustrating an example of a three-chamber type electrodialyzer.

[Method for Producing Formate and Method for Producing Formic Acid]

Embodiments of the invention are described in detail below.

A method for producing a formate according to an embodiment of the invention includes a first step of reacting hydrogen with carbon dioxide, a hydrogen carbonate or a carbonate using a catalyst in the presence of a solvent to form a formate in the reaction liquid, wherein the reaction is a two-phase system in which an organic phase and an aqueous phase are present in a separated state in the solvent, and a base concentration in the reaction is 2.5 mol/L or more.

A method for producing formic acid according to an embodiment of the invention includes a step of producing a formate by the above method, and a second step of protonating at least a part of the formate by electrodialysis to form formic acid and water.

<First Step>

In the embodiment of the invention, the first step is a step of reacting hydrogen with carbon dioxide, a hydrogen carbonate or a carbonate using a catalyst in the presence of a solvent to form a formate in the reaction liquid.

In the embodiment of the invention, the reaction of hydrogen with carbon dioxide, a hydrogen carbonate or a carbonate needs to be carried out in a two-phase system in which an organic phase and an aqueous phase are present in a separated state in the solvent.

Furthermore, the base concentration for the reaction needs to be 2.5 mol/L or more. By setting the base concentration to 2.5 mol/L or more, a formate at high concentration can be produced, and a formate can be produced with a high catalyst turnover number. The production cost can be suppressed by increasing the catalyst turnover number of a highly expensive catalyst, and a formate can be produced in high yield and with excellent productivity.

The reaction is preferably carried out in a catalyst solution (organic phase) in which a catalyst is dissolved in an organic solvent.

The formate formed in the reaction is dissolved in an aqueous solvent and is therefore eluted into the aqueous phase. For this reason, the reaction for forming the formate is prevented from being stopped by equilibrium, and the formate can be formed in high yield. Furthermore, since separation of the aqueous solution of the formate from the catalyst solution can be achieved by a simple method, it is difficult to deactivate the catalyst activity, a highly expensive catalyst can be reused, and high productivity can be realized.

When the method for producing a formate according to the embodiment of the invention is adopted, hydrogen and carbon dioxide can be stored as a formic acid alkali metal salt. A formate has a high hydrogen storage density, is safe and is stable as a chemical substance, and therefore, there are advantages such as that convenient handling can be achieved and hydrogen and carbon dioxide can be stored for a long time period.

A formate has high solubility in an aqueous solvent and can be fractionated as a high-concentration aqueous solution of a formate. Thus, after adjusting the formate concentration as necessary, the aqueous solution of the formate can be supplied to the second step.

The first step in the method for producing a formate according to the embodiment of the invention can be conducted, for example, as follows.

A reaction vessel equipped with a stirring device is provided, and a solvent is introduced into the reaction vessel. As necessary, a phase transfer catalyst may be further added. A catalyst is added to the reaction vessel and dissolved in a solvent to prepare a catalyst solution. Hydrogen and carbon dioxide, a hydrogen carbonate or a carbonate are introduced into the reaction vessel, and a reaction is conducted.

(Solvent)

The solvent according to the embodiment of the invention is not particularly limited so long as it can be obtained as a two-phase system in which an organic phase and an aqueous phase are present in a separated state in the reaction solution, and preferably contains a solvent that dissolves the catalyst to form a uniform solution.

The organic phase is a phase that contains an organic solvent as the solvent, and the aqueous phase is a phase that contains an aqueous solvent as the solvent.

The aqueous solvent includes, for example, water, methanol, ethanol, ethylene glycol, glycerin and mixed solvents thereof. Water is preferred from the standpoint of low environmental load.

The organic solvent includes, for example, toluene, benzene, xylene, propylene carbonate, dioxane, dimethyl sulfoxide, tetrahydrofuran, ethyl acetate, methylcyclohexane, cyclopentyl methyl ether and mixed solvents thereof, and the organic solvent is more preferably toluene or dioxane from the standpoint of separability from the aqueous solvent. That is, the organic phase preferably contains toluene or dioxane.

(Catalyst)

The catalyst according to the embodiment of the invention is not particularly limited but is preferably such that the catalyst turnover number: TON, which can be determined by the following calculation method, is 10000 or more.

TON is preferably 10,000 or more, more preferably 50,000 or more, and even more preferably 100,000 or more, from the standpoint of suppressing the production cost of the formate. Furthermore, since a higher TON is more preferred, the upper limit is not particularly limited and can be set to, for example, 10,000,000 or less.

TON calculation method:

$$TON=X/Y \quad \text{formula 1}$$

(In the formula 1, X represents the molar amount X (mol) of potassium formate formed by the following TON calculation reaction, a value of X is calculated by the following formula 2, and Y represents the molar amount (mol) of the catalyst used in the following reaction.)

$$X=(W/M)\times(Ia\times Ib/R)\times(A/B) \quad \text{formula 2}$$

(In the formula 2, W represents the amount (g) of dimethyl sulfoxide used for the quantification of potassium formate, M represents the molecular weight of dimethyl sulfoxide, R represents the ratio of the number of protons of dimethyl sulfoxide to the number of protons of potassium formate, Ia represents the proton NMR integration value of potassium formate, Ib represents the proton NMR integration value of dimethyl sulfoxide, A represents the mass (g) of the aqueous solution in the lower layer obtained by the following reaction, and B represents the mass (g) of the aqueous solution used for the quantification of potassium formate.)

TON calculation reaction:

(Production of Formate)

10 mmol of $KHCO_3$ was added to 1 mL of water in a glass vial equipped with a stirring rod in a glovebox under an inert gas, and then 0.12 μmol of a catalyst and 54 μmol of methyltrioctylammonium chloride were added to 1 mL of a solvent in which the catalyst obtains the highest TON and which is selected from toluene, dioxane, tetrahydrofuran, ethyl acetate, methylcyclohexane, and cyclopentyl methyl ether. Thereafter, the vial was placed in an autoclave, the autoclave was sealed and taken out of the glovebox.

The autoclave was heated to 90° C. while being stirred. When the temperature reached the target temperature, the autoclave was pressurized to 4.5 MPa with $H_2$. the reaction mixture was stirred for 18 hours, thereafter the reaction mixture was cooled with an ice bath, and pressure was carefully released.

An upper layer of the solution after the reaction was removed, and A g of an aqueous solution of a lower layer containing potassium formate and unreacted $KHCO_3$ was obtained.

(Quantification of Potassium Formate)

B g of the aqueous solution of the lower layer was collected and dissolved in 500 μL of deuterated water, W g of dimethyl sulfoxide was added as an internal standard, thereafter $^1H$ NMR analysis was performed, and the NMR integration value of potassium formate was designated as Ia, while the NMR integration value of dimethyl sulfoxide was designated as Ib.

For example, TON determined by the above-TON calculation method for the Ru catalyst 1 and Ru catalyst 7 used for the Examples of the invention are 66,000 for the Ru catalyst 1 and 56,000 for the Ru catalyst 7.

The catalyst used for the embodiment of the invention is preferably a catalyst that is dissolved in an organic solvent, more preferably a compound containing a metal element (metal element compound), and even more preferably a metal complex catalyst.

The metal element compound includes salts of metal elements with inorganic acids, such as a hydride salt, an oxide salt, a halide salt (chloride salt or the like), a hydroxide salt, a carbonic acid salt, a hydrogen carbonic acid salt, a sulfuric acid salt, a nitric acid salt, a phosphoric acid salt, a boric acid salt, a halogen acid salt, a perhalogen acid salt, a halous acid salt, a hypohalous acid salt, and a thiocyanic acid salt; salts of metal elements with organic acids, such as an alkoxide salt, a carboxylic acid salt (an acetic acid salt, a (meth)acrylic acid salt, or the like), and a sulfonic acid salt (a trifluoromethanesulfonic acid salt or the like); salts of metal elements with organic bases, such as an amide salt, a sulfonamide salt, and a sulfonimide salt (a bis(trifluoromethanesulfonyl)imide salt or the like); complex salts such as an acetylacetone salt, a hexafluoroacetylacetone salt, a porphyrin salt, a phthalocyanine salt, and a cyclopentadiene salt; and complexes or salts containing one or more of nitrogen compounds including a chain-like amine, a cyclic amine, an aromatic amine or the like, phosphorous compounds, compounds containing phosphorus and nitrogen, sulfur compounds, carbon monoxide, carbon dioxide, and water. These compounds may be either hydrates or anhydrides and are not particularly limited. Among these, a halide salt, a complex containing a phosphorus compound, a complex containing a nitrogen compound, and a complex or salt containing a compound containing phosphorus and nitrogen are preferred from the standpoint of further increasing the efficiency of forming formic acid.

These may be used singly, or two or more kinds may be used in combination.

A commercially available product can be used as the metal element compound, or a compound produced by a known method or the like can also be used. As the known method, for example, a method described in JP5896539B and methods described in Chem. Rev. 2017, 117, 9804-9838 and Chem. Rev. 2018, 118, 372-433 can be used.

The catalyst used for the method for producing a formate according to the embodiment of the invention is preferably a ruthenium complex represented by formula (1).

The ruthenium complex represented by the formula (1) is dissolved in an organic solvent and is insoluble in water. A formate formed by the reaction is easily dissolved in water. Therefore, the separation of the catalyst and the formate is easily achieved by a two-phase system reaction, the catalyst and the formate are respectively easily separated and recovered from the reaction system, and this enabled production of a formate in high yield.

According to the method of the present embodiment, a formate formed by the reaction can be separated from the catalyst by simple operation, and expensive catalyst can be reused.

The catalyst used in the embodiment of the invention is preferably at least one selected from a ruthenium complex represented by the following formula (1), a tautomer or stereoisomer thereof, and a salt compound of the complex, tautomer or stereoisomer.

[Chem. 3]

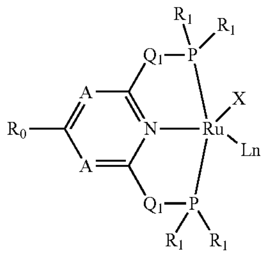

(1)

(In the formula (1), $R_0$ represents a hydrogen atom or an alkyl group, $Q_1$ each independently represents $CH_2$, NH or O, $R_1$ each independently represents an alkyl group or an aryl group (provided that when $Q_1$ represents NH or O, at least one of $R_1$ represents an aryl group), A each independently represents CH, $CR_5$ or N, $R_5$ represents an alkyl group, an aryl group, an aralkyl group, an amino group, a hydroxy group or an alkoxy group, X represents a halogen atom, n represents 0 to 3, and when more than one L are present, L each independently represents a neutral or anionic ligand.)

The $R_0$ in the formula (1) represents a hydrogen atom or an alkyl group. The alkyl group represented by $R_0$ includes a straight chain, branched or cyclic substituted or unsubstituted alkyl group.

The alkyl group represented by $R_0$ preferably includes an alkyl group having 1 to 30 carbon atoms, such as a methyl group, an ethyl group, an n-propyl group, an i-propyl group, a t-butyl group, an n-octyl group, an eicosyl group or a 2-ethylhexyl group. From the standpoint of easy procurement of raw materials, an alkyl group having 6 or fewer carbon atoms is preferred, and a methyl group is preferred.

The $R_0$ in the formula (1) is preferably a hydrogen atom or a methyl group.

$R_1$ in the formula (1) each independently represents an alkyl group or an aryl group, provided that when $Q_1$ represents NH or O, at least one of $R_1$ represents an aryl group. The alkyl group represented by $R_1$ includes a straight chain, branched or cyclic substituted or unsubstituted alkyl group. The alkyl group represented by $R_1$ preferably includes an alkyl group having 1 to 30 carbon atoms, such as a methyl group, an ethyl group, an n-propyl group, an i-propyl group, a t-butyl group, an n-octyl group, an eicosyl group or a 2-ethylhexyl group. From the standpoint of catalyst activity, an alkyl group having 12 or fewer carbon atoms is preferred, and a t-butyl group is preferred.

The aryl group represented by $R_1$ includes a substituted or unsubstituted aryl group having 6 to 30 carbon atoms, such as a phenyl group, a p-tolyl group, a naphthyl group, an m-chlorophenyl group or an o-hexadecanoylaminophenyl group. An aryl group having 12 or fewer carbon atoms is preferred, and a phenyl group is more preferred.

A each independently represents CH, $CR_5$ or N, and $R_5$ represents an alkyl group, an aryl group, an aralkyl group, an amino group, a hydroxy group or an alkoxy group.

The alkyl group represented by $R_5$ includes a straight chain, branched or cyclic substituted or unsubstituted alkyl group. The alkyl group represented by $R_5$ preferably includes an alkyl group having 1 to 30 carbon atoms, such as a methyl group, an ethyl group, an n-propyl group, an i-propyl group, a t-butyl group, an n-octyl group, an eicosyl group or a 2-ethylhexyl group. From the standpoint of easy procurement of raw materials, an alkyl group having 12 or fewer carbon atoms is preferred, and a methyl group is preferred.

The aryl group represented by $R_5$ includes a substituted or unsubstituted aryl group having 6 to 30 carbon atoms, such as a phenyl group, a p-tolyl group, a naphthyl group, an m-chlorophenyl group or an o-hexadecanoylaminophenyl group. An aryl group having 12 or fewer carbon atoms is preferred, and a phenyl group is more preferred.

The aralkyl group represented by $R_5$ includes a substituted or unsubstituted aralkyl group having 30 or less carbon atoms, such as a trityl group, a benzyl group, a phenethyl group, a tritylmethyl group, a diphenylmethyl group or a naphthylmethyl group, and is preferably an aralkyl group having 12 or fewer carbon atoms.

The alkoxy group represented by $R_5$ preferably includes a substituted or unsubstituted alkoxy group having 1 to 30 carbon atoms, such as a methoxy group, an ethoxy group, an isopropoxy group, a t-butoxy group, an n-octyloxy group or a 2-methoxyethoxy group.

X represents a halogen atom and is preferably a chlorine atom.

n represents an integer of 0 to 3 and represents the number of ligands coordinating to ruthenium. From the standpoint of stability of the catalyst, n is preferably 2 or 3.

When more than one L are present, L each independently represents a neutral or anionic ligand.

The neutral ligand represented by L includes, for example, ammonia, carbon monoxide, phosphines (for example, triphenylphosphine or tris(4-methoxyphenyl)phosphine), phosphine oxides (for example, triphenyl phosphine oxide), sulfides (for example, dimethyl sulfide), sulfoxides (for example, dimethyl sulfoxide), ethers (for example, diethyl ether), nitriles (for example, p-methylbenzonitrile), and heterocyclic compounds (for example, pyridine, N,N-dimethyl-4-aminopyridine, tetrahydrothiophene or tetrahydrofuran), and is preferably triphenylphosphine.

The anionic ligand represented by L includes, for example, a hydride ion (hydrogen atom), a nitrate ion and a cyanide ion, and is preferably a hydride ion (hydrogen atom).

In the formula (1), A preferably represents CH, and $Q_1$ preferably represents NH. Furthermore, n preferably represents 1 to 3, and L each independently preferably represents a hydrogen atom, carbon monoxide or triphenylphosphine.

The ruthenium complex represented by the formula (1) may be used singly alone and may be used as a mixture of two or more kinds.

The ruthenium complex represented by the formula (1) is preferably a ruthenium complex represented by the following formula (3).

[Chem. 4]

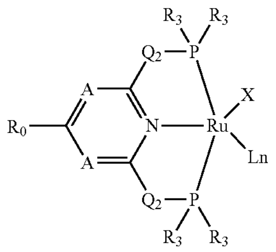

(3)

(In the formula (3), $R_0$ represents a hydrogen atom or an alkyl group, $Q_2$ each independently represents NH or O, $R_3$ each independently represents an aryl group, A each independently represents CH, $CR_5$ or N, $R_5$ represents an alkyl group, an aryl group, an aralkyl group, an amino group, a hydroxy group or an alkoxy group, X represents a halogen atom, n represents 0 to 3, and when more than one L are present, L each independently represents a neutral or anionic ligand.)

$R_0$, A, $R_5$, X, n and L in the formula (3) are synonymous with $R_0$, A, $R_5$, X, n and L in the formula (1), respectively, and preferred ranges thereof are also the same.

The aryl groups represented by $R_3$ in the formula (3) are each synonymous with the aryl group represented by $R_1$ in the formula (1), and the preferred ranges thereof are also the same.

Regarding the ruthenium complexes represented by the formula (1) and formula (3), ruthenium complexes produced by known methods can be used. As the known methods, for example, the methods described in E. Pidko et al., ChemCatChem 2014, 6, 1526-1530, and the like can be used.

The ruthenium complexes represented by the formula (1) and formula (3) may form stereoisomers due to coordination of a ligand or conformation, but may be a mixture of these stereoisomers or may be a single pure isomer.

Specific examples of the ruthenium complex, the ruthenium complexes represented by the formula (1) and formula (3), and the ligand include compounds listed below.

In the compounds listed below, tBu represents a tertiary butyl group, and Ph represents a phenyl group.

[Chem. 5]

1

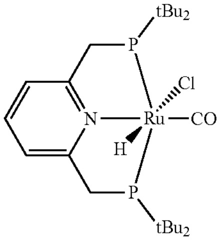

A

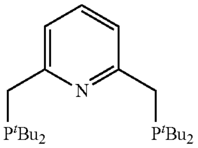

2

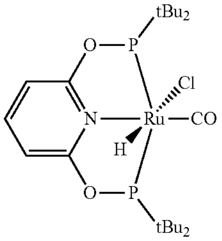

B

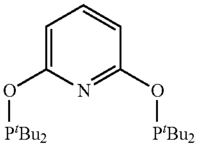

3

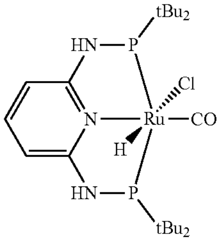

C

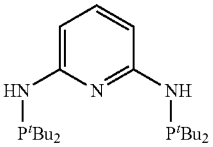

[Chem. 6]

5

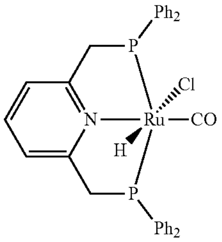

-continued

E

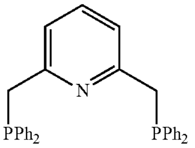

7

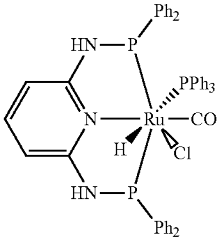

G

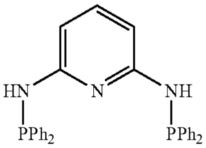

8

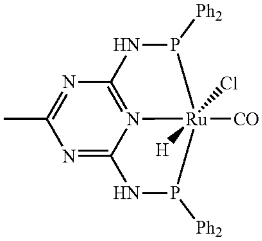

H

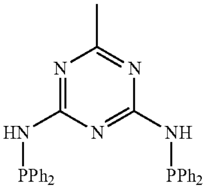

The amount of the catalyst (preferably a ruthenium complex) used is not particularly limited so long as a formate can be produced. The amount of the catalyst (preferably a ruthenium complex) used is preferably 0.1 μmol or more, more preferably 0.5 μmol or more, and still more preferably 1 μmol or more, per 1 L of the solvent, in order to sufficiently express the catalyst function. Furthermore, the amount of the catalyst used is preferably 1 mol or less, more preferably 10 mmol or less, and still more preferably 1 mmol or less, from the standpoint of cost. When two or more kinds of catalysts are used, the total amount of those used needs to be in the above range.

In the method for producing a formate according to the embodiment of the invention, the catalyst is preferably a metal complex catalyst, and the ligand of the metal complex catalyst is preferably present in excess in the reaction mixture. Therefore, the ligand of the complex used is preferably further added.

That is, in the method for producing a formate according to the embodiment of the invention, the catalyst is preferably a metal complex catalyst, and a ligand of the metal complex catalyst is preferably further added. For example, when the catalyst is a ruthenium complex represented by the formula (1), a ligand represented by the following formula (4) is preferably further added.

[Chem. 7]

(4)

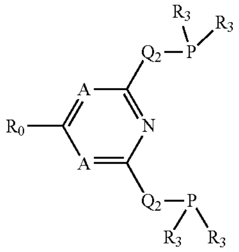

(In the formula (4), $R_0$ represents a hydrogen atom or an alkyl group, $Q_2$ each independently represents NH or O, $R_3$ each independently represents an aryl group, A each independently represents CH, $CR_5$ or N, and $R_5$ represents an alkyl group, an aryl group, an aralkyl group, an amino group, a hydroxy group or an alkoxy group.)

$R_0$, $Q_2$, $R_3$, A and $R_5$ in the formula (4) are synonymous with $R_0$, $Q_2$, $R_3$, A, and $R_5$ in the formula (3), respectively, and preferred ranges thereof are also the same.

By adding the ligand for forming a complex to the reaction system in excess, even when the ligand is oxidized and deteriorated by oxygen and impurities included in the system, the deteriorated ligand and the added ligand are exchanged to restore the catalyst function, and therefore, stability of the catalyst can be improved.

Addition of the ligand represented by the above formula (4) into the reaction mixture may be carried out when the reaction mixture is prepared or may be carried out in the middle of the reaction. However, from the standpoint of process management, the addition is preferably carried out when the reaction mixture is prepared.

(Phase Transfer Catalyst)

The method for producing formic acid according to the embodiment of the invention requires to conduct the reaction in a two-phase system. Therefore, a phase transfer catalyst may be used in order to smoothly perform the transfer of a substance between two phases. The phase transfer catalyst includes, for example, a quaternary ammonium salt, a quaternary phosphate, a macrocyclic polyether such as a crown ether, a nitrogen-containing macrocyclic polyether such as a cryptand, a nitrogen-containing chain polyether, polyethylene glycol and an alkyl ether thereof. Above all, a quaternary ammonium salt is preferred from the standpoint that mass transfer between an aqueous solvent and an organic solvent is easy even under mild reaction conditions.

The quaternary ammonium salt includes, for example, methyltrioctylammonium chloride, benzyltrimethylammonium chloride, trimethylphenylammonium bromide, tributylammonium tribromide, tetrahexylammonium hydrogen sulfate, decyltrimethylammonium bromide, diallyldimethylammonium chloride, dodecyltrimethylammonium bromide, dimethyldioctadecylammonium bromide, tetraethylammonium tetrafluoroborate, ethyltrimethylammonium iodide tris(2-hydroxyethyl)methylammonium hydroxide, tetramethylammonium acetate, tetramethylammonium bromide, and tetraethylammonium iodide. Methyltrioctylammonium chloride is preferred.

The amount of the phase transfer catalyst used is not particularly limited so long as a formate can be produced.

The amount of the phase transfer catalyst used is preferably 0.1 mmol or more, more preferably 0.5 mmol or more and still more preferably 1 mmol or more, per 1 L of the solvents of the organic phase and aqueous phase for the purpose of efficiently supporting the transfer of a carbonate or a hydrogen carbonate. Furthermore, from the standpoint of cost, the amount is preferably 1 mol or less, more preferably 500 mmol or less and still more preferably 100 mmol or less. When two or more kinds of the phase transfer catalysts are used, the total amount of those needs to be in the above range.

(Carbon Dioxide and Hydrogen)

As hydrogen used in the embodiment of the invention, either a hydrogen gas cylinder or liquid hydrogen can be used. As a hydrogen supply source, for example, hydrogen generated during a smelting process of iron manufacture, hydrogen generated during a soda manufacturing process, and the like can be used. Furthermore, hydrogen generated from electrolysis of water can be used.

Carbon dioxide used in the embodiment of the invention may be pure carbon dioxide gas or may be a mixed gas containing a component other than carbon dioxide. Carbon dioxide gas and other gas may be separately introduced, and a mixed gas may be formed beforehand and introduced.

The component other than carbon dioxide includes an inert gas such as nitrogen or argon, water vapor, and any optional component contained in an exhaust gas or the like.

As the carbon dioxide, a carbon dioxide gas cylinder, liquid carbon dioxide, supercritical carbon dioxide, dry ice, and the like can be used.

Hydrogen gas and carbon dioxide gas may be introduced into the reaction system each alone or may be introduced as a mixed gas.

The proportions of hydrogen and carbon dioxide used are preferably such that the proportions are equal amounts on a molar basis or hydrogen is in excess.

When a hydrogen cylinder is used as the hydrogen used in the method for producing formic acid according to the embodiment of the invention, the pressure is preferably 0.1 MPa or more, more preferably 0.2 MPa or more and still more preferably 0.5 MPa or more, from the standpoint of sufficiently securing reactivity. Furthermore, the pressure is preferably 50 MPa or less, more preferably 20 MPa or less and still more preferably 10 MPa or less, from the standpoint that facilities are liable to become large.

The pressure of carbon dioxide used in the method for producing formic acid according to the embodiment of the invention is preferably 0.1 MPa or more, more preferably 0.2 MPa or more and still more preferably 0.5 MPa or more, from the standpoint of sufficiently securing reactivity. Furthermore, the pressure is preferably 50 MPa or less, more preferably 20 MPa or less and still more preferably 10 MPa or less, from the standpoint that facilities are liable to become large.

Hydrogen gas and carbon dioxide gas may be introduced into a catalyst solution by bubbling (blowing). Furthermore, after introducing a gas including hydrogen gas and carbon dioxide gas, the catalyst solution, hydrogen gas and carbon dioxide gas may be stirred by stirring with a stirring device or by rotating the reaction vessel.

A method for introducing carbon dioxide, hydrogen, a catalyst, a solvent and the like that are used for the reaction into the reaction vessel is not particularly limited. All of the raw materials may be introduced at once, a part or all of the raw materials may be introduced stepwise, or a part or all of the raw materials may be introduced continuously. Furthermore, the method may be an introduction method combining those methods.

(Hydrogen Carbonate and Carbonate)

The hydrogen carbonate and carbonate used in the embodiment of the invention include a carbonate or hydrogen carbonate of an alkali metal.

The hydrogen carbonate includes, for example, sodium hydrogen carbonate and potassium hydrogen carbonate. Potassium hydrogen carbonate is preferred from the standpoint of high solubility in water.

The carbonate includes, for example, sodium carbonate, potassium carbonate, sodium potassium carbonate and sodium sesquicarbonate.

In the first step, the base concentration (base concentration in the aqueous phase) in the reaction of hydrogen with carbon dioxide, a hydrogen carbonate or a carbonate needs to be 2.5 mol/L or more, as described above.

The base concentration for the reaction is preferably 2.5 mol/L or more, more preferably 5 mol/L or more, and still more preferably 10 mol/L or more, from the standpoint of increasing the maximum amount of production of the formate. Furthermore, in order to suppress a decrease in the stirring efficiency of the reaction due to an excessive increase in the amount of a precipitated salt derived from the base, the base concentration is preferably 30 mol/L or less, more preferably 25 mol/L or less, and still more preferably 20 mol/L or less.

(Reaction Conditions)

The reaction conditions in the method for producing a formate according to the embodiment of the invention are not particularly limited, and the reaction conditions can be appropriately changed during the reaction process. The form of the reaction vessel used for the reaction is not particularly limited.

The reaction temperature is not particularly limited. However, to efficiently proceed the reaction, the temperature is preferably 30° C. or higher, more preferably 40° C. or higher and still more preferably 50° C. or higher. Furthermore, from the standpoint of energy efficiency, the reaction temperature is preferably 200° C. or lower, more preferably 150° C. or lower and still more preferably 100° C. or lower.

The reaction time is not particularly limited. However, for example, the reaction time is preferably 0.5 hours or more, more preferably 1 hour or more, and still more preferably 2 hours or more, from the standpoint of sufficiently securing the amount of formic acid formed. Furthermore, the reaction time is preferably 24 hours or less, more preferably 20 hours or less, and still more preferably 18 hours or less, from the standpoint of cost.

The concentration of the formate (concentration of the formate in the aqueous phase) formed by the first step is preferably 2.5 mol/L or more, more preferably 5 mol/L or more, and still more preferably 10 mol/L or more, in order to increase the TON and produce the formate in high yield and with excellent productivity. Furthermore, in order to simplify the production process by producing the formate in a dissolved state, the concentration of the formate is preferably 30 mol/L or less, more preferably 25 mol/L or less, and still more preferably 20 mol/L or less.

<Second Step>

A second step is a step of protonating at least a part of the formate by electrodialysis to form formic acid and water.

The method for producing formic acid according to the embodiment of the invention preferably includes a step of producing a formate by the method for producing a formate according to the embodiment of the invention, and the second step.

In the embodiment of the invention, since the formate formed in the first step is eluted into the aqueous phase, an aqueous solution of formate is obtained by fractionating the aqueous phase.

Formic acid is preferably formed by separating the aqueous phase in the first step and treating the obtained aqueous solution of formate using an electrodialyzer by the second step. The aqueous phase to be separated is the aqueous phase after completion of the first step.

In the second step, the aqueous solution of formate obtained by the first step as described above may be used as it is, or the formate concentration may be adjusted by concentrating or diluting the solution as necessary and used.

A method for diluting an aqueous solution of a formate includes a method of diluting the solution by adding pure water.

A method for concentrating an aqueous solution of a formate includes a method of distilling off water from the aqueous solution of formate, a method of concentrating the aqueous solution of formate using a separation membrane unit equipped with a reverse osmosis membrane, and the like.

During the treatment using an electrodialyzer, it is preferable to separate the aqueous phase in the first step, adjust the concentration of the formate in the aqueous phase by dilution and then use the aqueous phase in the second step, from the standpoint of suppressing the formate loss caused by a phenomenon of concentration diffusion of a high concentration aqueous solution of a formate.

When an aqueous solution of a formate with high concentration is obtained by the first step, the formate concentration is adjusted by diluting to a concentration appropriate for electrodialysis, and then the aqueous solution of formate is supplied to the second step, TON is further increased, and formic acid can be produced in higher yield and with more excellent productivity.

The degree of preparation (preferably dilution) of the concentration of the aqueous solution of formate obtained in the first step can be appropriately selected. The concentration of a formate in the aqueous solution of formate after concentration adjustment is preferably a concentration appropriate for electrodialysis, preferably 2.5 mol/L or more, more preferably 3 mol/L or more, and still more preferably 5 mol/L or more. Furthermore, the concentration is preferably 20 mol/L or less, more preferably 15 mol/L or less, and still more preferably 10 mol/L or less, from the standpoint of suppressing the formate loss caused by a phenomenon of concentration diffusion of the high-concentration aqueous solution of formate during a treatment using an electrodialyzer.

Pure water can be used for dilution. Furthermore, the water formed in the second step may be used for dilution. It is preferable to reuse the water formed by the second step during dilution because there are advantages such as that the cost required for waste water treatment and the environmental load can be reduced.

In the method for producing formic acid according to the embodiment of the invention, the aqueous solution of formate obtained by the first step may be reused in the second step after adding acid to the solution and conducting a decarbonation treatment. That is, the aqueous phase in the first step is separated, acid is added to conduct a decarbonation treatment, and then the aqueous phase may be used in the second step.

The aqueous solution of formate obtained by the first step may include unreacted carbonate and hydrogen carbonate formed by side reactions, and when the solution containing carbonate and hydrogen carbonate is electrodialyzed, there is a risk that carbon dioxide may be generated, and the dialysis efficiency may be decreased. Therefore, by adding acid to the aqueous solution of formate obtained by the first step, conducting a decarbonation treatment and then electrodialyzing the solution, TON can be further increased, and formic acid can be produced in higher yield with more excellent productivity.

The acid used for the decarbonation treatment includes, for example, formic acid, citric acid, acetic acid, malic acid, lactic acid, succinic acid, tartaric acid, butyric acid, fumaric acid, propionic acid, hydrochloric acid, nitric acid and sulfuric acid. Formic acid is preferably used.

Regarding the amount of the acid used, the amount of the acid used is preferably 50% or more, and more preferably 80% or more, with respect to the amount of carbonic acid present in the solution, from the standpoint of suppressing the amount of carbonic acid generated during the electrodialysis treatment. Furthermore, from the standpoint of suppressing deterioration of the electrodialyzer by making the pH of the formate solution neutral during the electrodialysis treatment, the amount of the acid used is preferably 150% or less, and more preferably 120% or less, with respect to the amount of carbonic acid present in the solution.

In the embodiment of the invention, the proportion of the formate that is protonated by the second step is such that the proportion to be protonated is preferably 10% or more, the proportion to be protonated is more preferably 20% or more, and the proportion to be protonated is still more preferably 30% or more, with respect to the initial molar amount of the formate in the aqueous solution of formate, from the standpoint of increasing the purity of the aqueous solution of formic acid recovered.

The electrodialyzer includes a two-chamber type electrodialyzer that uses a bipolar membrane and an anionic exchange membrane or a cationic exchange membrane, a three-chamber type electrodialyzer that uses a bipolar membrane, an anionic exchange membrane and a cationic exchange membrane, and the like.

FIG. 1 is a schematic diagram showing an example of a three-chamber type electrodialyzer. The electrodialyzer shown in FIG. 1 is equipped with more than one bipolar membranes, more than one anionic exchange membranes, and more than cationic exchange membranes, respectively, and these bipolar membranes, anionic exchange membranes and cationic exchange membranes are disposed between an anode and a cathode, forming a base tank, a sample tank (salt tank) and an acid tank. As an aqueous solution of a formate is circulated and supplied to the sample tank while passing electricity, the formate is gradually converted to formic acid, formic acid is recovered from the acid tank, water is recovered from the sample tank, and hydroxide is recovered from the base tank.

A two-chamber type electrodialyzer is equipped with more than one bipolar membranes and more than one cationic exchange membranes, respectively, and these bipolar membranes and cationic exchange membranes are alternately disposed between an anode and a cathode. Each salt chamber is formed between each bipolar membrane and a cationic exchange membrane disposed on the cathode side thereof, while a base tank is formed between each bipolar membrane and a cationic exchange membrane disposed on the anode side thereof. By circulating and supplying an aqueous solution of a formate to the salt chamber while passing electricity, the formate circulated and supplied to the salt chamber is gradually converted to formic acid while forming hydroxide in the base tank.

A formic acid solution can be obtained by protonating the formate by a simple method by the second step.

[Formate Production System and Formic Acid Production System]

A formate production system according to the embodiment of the invention includes a formate production apparatus that reacts hydrogen with carbon dioxide, a hydrogen carbonate or a carbonate to form a formate in the reaction liquid, the reaction is a two-phase system in which an organic phase and an aqueous phase are present in a separated state in the solvent, and the base concentration for the reaction is 2.5 mol/L or more.

The formic acid production system according to the embodiment of the invention may also include an electrodialyzer that protonates at least a part of the formate by electrodialysis to form formic acid, in addition to the formate production system.

The formic acid production system according to the embodiment of the invention may further include an apparatus that adjusts the concentration of the formate in the aqueous phase by dilution, and the apparatus may be a diluting apparatus.

The formic acid production system according to the embodiment of the invention may be equipped with a formate production apparatus 10 and an electrodialyzer 30, and the products obtained by each apparatus may be supplied to another apparatus after transportation or storage.

Figure 2:
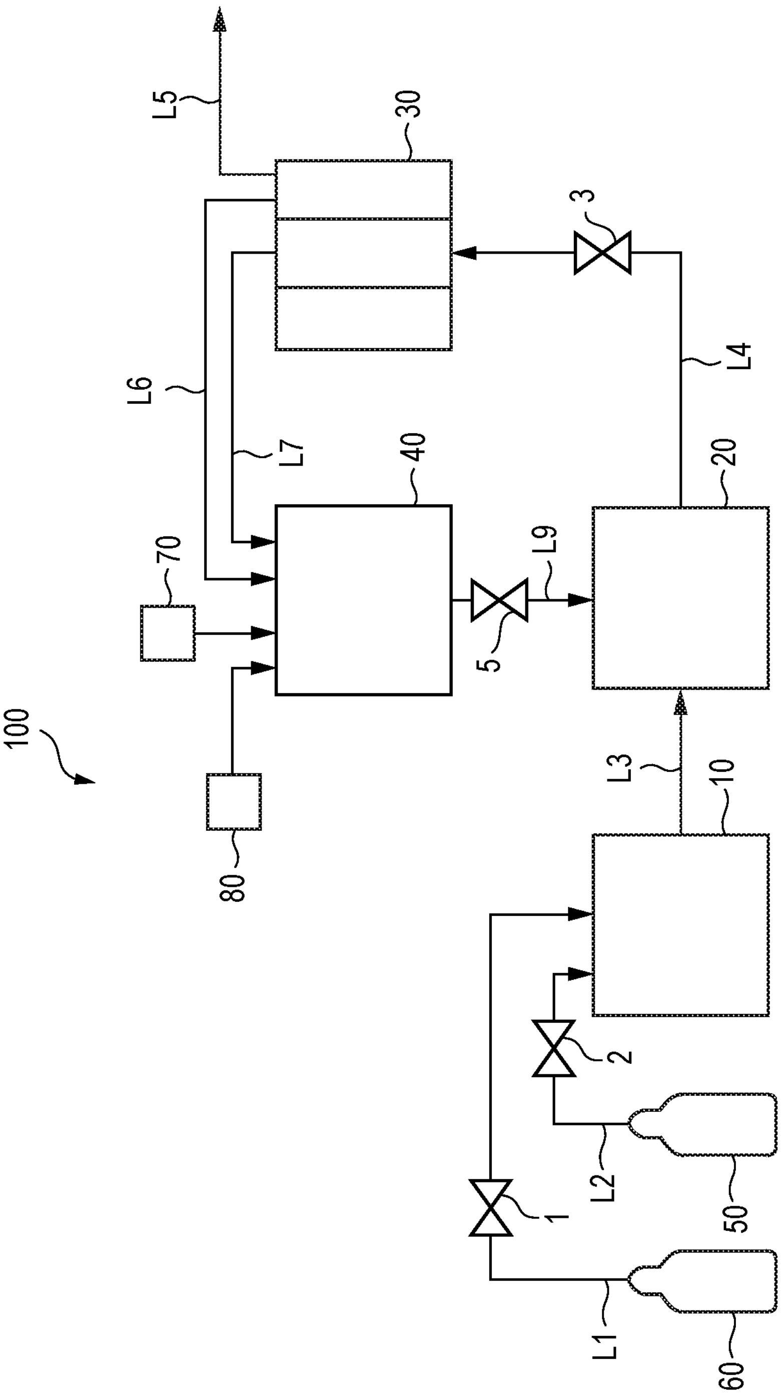
FIG. 2 is a schematic outline diagram illustrating an example of a formic acid production system according to an embodiment of the invention.

FIG. 2 is a diagram showing an example of the formic acid production system according to the embodiment of the invention.

The formic acid production system 100 shown in FIG. 2 may be equipped with a formate production apparatus 10 and an electrodialyzer 30 and may be further equipped with a diluting apparatus 20 and a diluting water storage unit 40.

The formic acid production system 100 may be further equipped with a carbon dioxide cylinder 60 that introduces carbon dioxide into the formate production apparatus 10, and a hydrogen cylinder 50 that introduces hydrogen into the formate production apparatus 10. The concentrations and pressures of carbon dioxide and hydrogen can be adjusted by a valve 1 and a valve 2 provided in a pipe L1 and a pipe L2.

The formate produced in the formate production apparatus 10 is supplied to the electrodialyzer 30 as an aqueous solution of a formate by separating the aqueous phase. However, the aqueous solution of formate may be delivered to the diluting apparatus 20 by a flow channel L3 as shown in FIG. 2, and the formate concentration in the aqueous phase may be adjusted by dilution.

In the formic acid solution in which the formate concentration has been adjusted by the diluting apparatus 20, at least a part of the formate is protonated by the electrodialyzer 30, and formic acid and water are formed. The formic acid formed can be taken out by a flow channel L5. Furthermore, the water formed may be delivered to the diluting water storage unit 40 by a flow channel L7.

In the diluting water storage unit 40, a part of the formic acid formed by the electrodialyzer 30 may be delivered to the diluting water storage unit 40 by a flow channel L6. The diluting water storage unit 40 may be equipped with a water supply unit 70 and a formic acid supply unit 80, and an aqueous solution of formic acid adjusted in the diluting water storage unit 40 may be supplied to the diluting apparatus 20 by a flow channel L9 to be subjected to a decarbonation treatment.

Each flow channel may be equipped with a value that adjusts pressure or the supply amount.

According to the method for producing a formate, the method for producing formic acid, the formate production system and the formic acid production system according to the present embodiment, a formate and formic acid can be produced in high yield and with excellent productivity.

[Method for Producing Antifreezing Agent]

A method for producing an antifreezing agent of the present embodiment preferably includes a step of producing a formate by the method for producing a formate of the present embodiment.

The formate obtained by the method for producing a formate of the present embodiment and the formate production system can be used not only as a hydrogen storage material but also in the conventional use applications such as oil field excavation, leather tanning, livestock feed and antifreezing agents. Therefore, the formate can contribute to the problems of global warming and fossil fuel depletion.

For example, regarding the use applications of the antifreezing agent, a formate is attracting attention as a non-chloride-based antifreezing agent for the purpose of preventing salt damage, which is a problem with calcium chloride and the like. The formate that is used for the antifreezing agent includes sodium formate, potassium formate and the like. Since potassium formate has higher solubility in water than sodium formate, sodium formate has a feature of being easily dried as a powder from the aqueous solution obtained by the method for producing a formate and the formate production system of the present embodiment. Therefore, when it is wished to spray the antifreezing agent in a powder form or a granular form, sodium formate is preferred. In contrast, when the antifreezing agent is sprayed as an aqueous solution, potassium formate that can dissolve at high concentration has a feature that an antifreezing effect relative to a unit spraying amount is likely to be obtained.

The formate obtained by the method for producing a formate and the formate production system of the present embodiment may include unreacted carbonate, hydrogen carbonate, and the like. Since the carbonate and hydrogen carbonate do not exhibit an antifreezing effect, the antifreezing effect can be enhanced by neutralizing a part or all of the carbonate and hydrogen carbonate present by using an acid.

The acid used for neutralization may be the acid used for the decarbonation treatment of the aqueous solution of formate obtained by the above first step. Preferably, the environmental performance of the antifreezing agent obtained can be enhanced by using an acid derived from a non-fossil fuel. Examples include formic acid obtained by the method for producing formic acid of the invention, and citric acid, acetic acid, lactic acid, succinic acid and tartaric acid, which are produced from farm products or by fermentation. At least one or more acids selected from the group consisting of formic acid and acetic acid are preferred. That is, the method for producing an antifreezing agent of the present embodiment preferably further includes a step of adding at least one or more acids selected from the group consisting of formic acid and acetic acid to a formate.

EXAMPLES

The invention is described in detail below by reference to Examples and Comparative Examples. However, it should be understood that the invention is not limited to those Examples.

Synthesis of Catalyst

(Synthesis Example 1) Synthesis of Ru Catalyst 1

Ru catalyst 1 was synthesized by the following operation.

40 mg (0.1 mmol) of a ligand A shown below was added to a THE (tetrahydrofuran) (5 ml) suspension of 95.3 mg (0.1 mmol) of $[RuHCl(PPh_3)_3(CO)]$ in an inert atmosphere, the resulting mixture was stirred and heated at 65° C. for 3 hours to conduct a reaction. Thereafter, the resulting reaction mixture was cooled to room temperature (25° C.).

A yellow solution obtained was filtered, and the filtrate was evaporated to dryness under a vacuum. Yellow residual oil obtained was dissolved in a very small amount of THF (1 mL), hexane (10 mL) was slowly added to the resulting solution to precipitate a yellow solid, and the solid was filtered and dried under vacuum. Thus, Ru catalyst 1 (55 mg, 97%) as yellow crystals was obtained. In the Ru ruthenium catalyst 1 and ligand A shown below, tBu indicates a tertiary butyl group.

[Chem. 8]

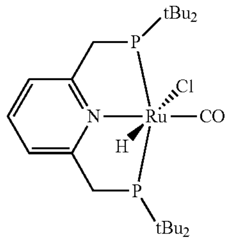

1

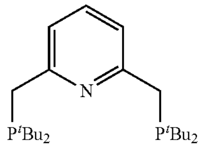

A $^{31}P\{^1H\}(C_6D_6)$: 90.8 (s), $^1H(C_6D_6)$:-14.54 (t, 1H, J=20.0 Hz), 1.11 (t, 18H, J=8.0 Hz), 1.51 (t, 18H, J=8.0 Hz), 2.88 (dt, 2H, J=16.0 Hz, J=4.0 Hz), 3.76 (dt, 2H, J=16.0 Hz, J=4.0 Hz), 6.45 (d, 2H, J=8.0 Hz), 6.79 (t, 1H, J=8.0 Hz).

$^{13}C\{^1H\}NMR(C_6D_6)$: 29.8 (s), 30.7 (s), 35.2 (t, J=9.5 Hz), 37.7 (t, J=6.0 Hz), 37.9 (t, J=6.5 Hz), 119.5 (t, J=4.5 Hz), 136.4 (s), 163.4 (t, J=5.0 Hz), 209.8 (s).

(Synthesis Example 2) Synthesis of Ru Catalyst 7

Ru catalyst 7 was synthesized by the following operation.

142.6 mg of a ligand G and 284.6 mg of $[RuHCl(PPh_3)_3(CO)]$ were mixed with 5 mL of benzene in an inert atmosphere, and the resulting suspension was refluxed one night. A yellow precipitate formed was collected on a filter and cleaned with 5 mL of ether 4 times.

The precipitate was dried in a vacuum, and 154.0 mg of Ru catalyst 7 was obtained.

In the Ru catalyst 7 and ligand G shown below, Ph indicates a phenyl group.

[Chem. 9]

7

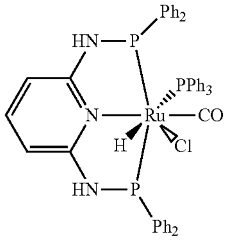

G

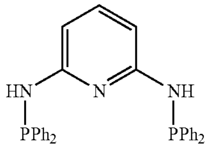

$^{31}P\{^1H\}NMR(CDC_3)$:95.58 (br, s), 29.71 (s).

$^1H$ NMR (400 MHz, $CD_2Cl_2$) δ9.92 (s, 2H), 8.11 (q, J=6.6 Hz, 4H), 7.38-7.24 (m, 4H), 7.20 (t, J=7.5 Hz, 3H), 7.16-7.04 (m, 4H), 7.04-6.92 (m, 14H), 6.87 (td, J=7.6, 2.1 Hz, 6H), 6.51 (d, J=8.0 Hz, 1H), 6.61 (d, J=8.0 Hz, 2H), −7.22 (dt, J=89.2, 23.1 Hz, 1H).

Example 1

(Formate Forming Reaction)

1 mL of water was weighed out and put in a glass vial equipped with a stirring rod in a glovebox under an inert gas, 2.5 mmol of potassium hydrogen carbonate was added thereto, and thereafter 0.12 μmol of the Ru catalyst 1 and 54 μmol of methyltrioctylammonium chloride were added to 1 mL of toluene. Thereafter, the vial was placed in an autoclave, and the autoclave was sealed and taken out of the glovebox. The autoclave was heated to 90° C. while being stirred. When the temperature reached the target temperature, the autoclave was pressurized to 4.5 MPa with hydrogen. The reaction mixture was stirred for 2.5 hours, thereafter the reaction mixture was cooled with an ice bath, and pressure was carefully released. An upper layer of the solution after the reaction was removed, and an aqueous solution of a lower layer containing potassium formate and unreacted potassium hydrogen carbonate remained. 100 μL of the aqueous solution of the lower layer was collected and dissolved in 500 μL of deuterated water, 300 μL of dimethyl sulfoxide was added as an internal standard, and then $^1H$ NMR was measured. Thus, calculation of the TON of the catalyst and the potassium hydrogen carbonate-converted formate formation efficiency was conducted. As a result, the TON of the catalyst was 13000, and the potassium hydrogen carbonate-converted formate formation efficiency was 0.64.

(Formate Protonation Reaction)

14 g of potassium hydroxide dissolved in 500 mL of water was charged into a base tank. 105.15 g of potassium formate dissolved in 500 mL of water was charged into a salt tank. 500 mL of ion-exchanged water was charged into an acid tank. When the electrodialyzer was started, a voltage of 28 V and a current of 0.24 A were reached, and the electrical conductivity of the salt tank at that time was 154.1 S/m. As a dialysis treatment was conducted, the electrical conductivity gradually decreased, and after 87 minutes, the electrical conductivity reached 0. Thus, the dialysis treatment was ended. Furthermore, the voltage at that time was 28.0 V, and the current was 0.87 A. The amount of the solution (salt liquid) in the salt tank after completion of dialysis was 350 mL, the amount of the solution (acid liquid) in the acid tank was 556 mL, and the liquid (base liquid) in the base tank was 595 mL. 100 μL of the acid liquid was collected and dissolved in 500 μL of deuterated water, 300 μL of dimethyl sulfoxide was added as an internal standard, and $^1H$ NMR was measured to quantitatively determine formic acid in the acid liquid after completion of dialysis. Furthermore, the formic acid recovery rate in the acid liquid was calculated, and as a result, it was found that the yield was 0.85. Furthermore, in order to perform quantification of potassium in the acid liquid after completion of dialysis, 20 mg of the acid liquid was collected and diluted to 50.5 times with water, the dilution was measured with a potassium ion meter, and then the ratio (formic acid/(potassium formate+formic acid)) in the acid liquid was calculated, which was found to be 0.98.

Finally, from the results of examination of the formate forming reaction and the formate protonation reaction, the potassium hydrogen carbonate-converted formic acid recovery rate was 0.54.

Example 2

(Formate Forming Reaction)

1 mL of water was weighed out and put in a glass vial equipped with a stirring rod in a glovebox under an inert gas, 5 mmol of potassium hydrogen carbonate was added thereto, and thereafter 0.12 μmol of the Ru catalyst 1 and 54 μmol of methyltrioctylammonium chloride were added to 1 mL of toluene. Thereafter, the vial was placed in an autoclave, and the autoclave was sealed and taken out of the glovebox. The autoclave was heated to 90° C. while being stirred. When the temperature reached the target temperature, the autoclave was pressurized to 4.5 MPa with hydrogen. The reaction mixture was stirred for 2.5 hours, thereafter the reaction mixture was cooled with an ice bath, and pressure was carefully released. An upper layer of the solution after the reaction was removed, and an aqueous solution of a lower layer containing potassium formate and unreacted potassium hydrogen carbonate remained. 100 μL of the aqueous solution of the lower layer was collected and dissolved in 500 μL of deuterated water, 300 μL of dimethyl sulfoxide was added as an internal standard, and then $^1H$ NMR was measured. Thus, calculation of the TON of the catalyst and the potassium hydrogen carbonate-converted formate formation efficiency was conducted. As a result, the TON of the catalyst was 27500, and the potassium hydrogen carbonate-converted formate formation efficiency was 0.66.

(Formate Protonation Reaction)

14 g of potassium hydroxide dissolved in 500 mL of water was charged into a base tank. 210.3 g of potassium formate dissolved in 500 mL of water was charged into a salt tank. 500 mL of ion-exchanged water was charged into an acid tank. When the electrodialyzer was started, a voltage of 28 V and a current of 0.28 A were reached, and the electrical conductivity of the salt tank at that time was 229.8 S/m. As a dialysis treatment was conducted, the electrical conductivity gradually decreased, and after 137 minutes, the electrical conductivity reached 0. Thus, the dialysis treatment was ended. Furthermore, the voltage at that time was 28.0 V, and the current was 1.29 A. The amount of the solution (salt solution) in the salt tank after completion of dialysis was 275 mL, the amount of the solution (acid liquid) in the acid tank was 590 mL, and the liquid (base solution) in the base tank was 685 mL. 100 μL of the acid liquid was collected and dissolved in 500 μL of deuterated water, 300 μL of dimethyl sulfoxide was added as an internal standard, and $^1$H NMR was measured to quantitatively determine formic acid in the acid liquid after completion of dialysis. Furthermore, the formic acid recovery rate in the acid liquid was calculated, and as a result, it was found that the yield was 0.90. Furthermore, in order to perform quantification of potassium in the acid liquid after completion of dialysis, 20 mg of the acid liquid was collected and diluted to 50 times with water, the dilution was measured with a potassium ion meter, and then the ratio (formic acid/(potassium formate+formic acid)) in the acid liquid was calculated, which was found to be 0.99.

Finally, from the results of examination of the formate forming reaction and the formate protonation reaction, the potassium hydrogen carbonate-converted formic acid recovery rate was 0.59.

Example 3

(Formate Forming Reaction)

1 mL of water was weighed out and put in a glass vial equipped with a stirring rod in a glovebox under an inert gas, 10 mmol of potassium hydrogen carbonate was added thereto, and thereafter 0.12 μmol of the Ru catalyst 1 and 54 μmol of methyltrioctylammonium chloride were added to 1 mL of toluene. Thereafter, the vial was placed in an autoclave, and the autoclave was sealed and taken out of the glovebox. The autoclave was heated to 90° C. while being stirred. When the temperature reached the target temperature, the autoclave was pressurized to 4.5 MPa with hydrogen. The reaction mixture was stirred for 2.5 hours, thereafter the reaction mixture was cooled with an ice bath, and pressure was carefully released. An upper layer of the solution after the reaction was removed, and an aqueous solution of a lower layer containing potassium formate and unreacted potassium hydrogen carbonate remained. 100 μL of the aqueous solution of the lower layer was collected and dissolved in 500 μL of deuterated water, 300 μL of dimethyl sulfoxide was added as an internal standard, and then $^1$H NMR was measured. Thus, calculation of the TON of the catalyst and the potassium hydrogen carbonate-converted formate formation efficiency was conducted. As a result, the TON of the catalyst was 65000, and the potassium hydrogen carbonate-converted formate formation efficiency was 0.78.

(Formate Protonation Reaction)

14 g of potassium hydroxide dissolved in 500 mL of water was charged into a base tank. 210.3 g of potassium formate that was dissolved in 250 mL of water then diluted and adjusted with a two-fold amount of water by further charging 250 mL of water, was charged into a salt tank. 500 mL of ion-exchanged water was charged into an acid tank. When the electrodialyzer was started, a voltage of 28 V and a current of 0.28 A were reached, and the electrical conductivity of the salt tank at that time was 230.0 S/m. As a dialysis treatment was conducted, the electrical conductivity gradually decreased, and after 140 minutes, the electrical conductivity reached 0. Thus, the dialysis treatment was ended. Furthermore, the voltage at that time was 28.0 V, and the current was 1.30 A. The amount of the solution (salt solution) in the salt tank after completion of dialysis was 280 mL, the amount of the solution (acid liquid) in the acid tank was 590 mL, and the liquid (base solution) in the base tank was 680 mL. 100 μL of the acid liquid was collected and dissolved in 500 μL of deuterated water, 300 μL of dimethyl sulfoxide was added as an internal standard, and $^1$H NMR was measured to quantitatively determine formic acid in the acid liquid after completion of dialysis. Furthermore, the formic acid recovery rate in the acid liquid was calculated, and as a result, it was found that the yield was 0.89. Furthermore, in order to perform quantification of potassium in the acid liquid after completion of dialysis, 20 mg of the acid liquid was collected and diluted to 50 times with water, the dilution was measured with a potassium ion meter, and then the ratio (formic acid/(potassium formate+formic acid)) in the acid liquid was calculated, which was found to be 0.99.

Finally, from the results of examination of the formate forming reaction and the formate protonation reaction, the potassium hydrogen carbonate-converted formic acid recovery rate was 0.69.

Example 4

(Formate Forming Reaction)

1 mL of water was weighed out and put in a glass vial equipped with a stirring rod in a glovebox under an inert gas, 14 mmol of potassium hydrogen carbonate was added thereto, and thereafter 0.12 μmol of the Ru catalyst 1 and 54 μmol of methyltrioctylammonium chloride were added to 1 mL of toluene. Thereafter, the vial was placed in an autoclave, and the autoclave was sealed and taken out of the glovebox. The autoclave was heated to 90° C. while being stirred. When the temperature reached the target temperature, the autoclave was pressurized to 4.5 MPa with hydrogen. The reaction mixture was stirred for 2.5 hours, thereafter the reaction mixture was cooled with an ice bath, and pressure was carefully released. An upper layer of the solution after the reaction was removed, and an aqueous solution of a lower layer containing potassium formate and unreacted potassium hydrogen carbonate remained. 100 μL of the aqueous solution of the lower layer was collected and dissolved in 500 μL of deuterated water, 300 μL of dimethyl sulfoxide was added as an internal standard, and then $^1$H NMR was measured. Thus, calculation of the TON of the catalyst and the potassium hydrogen carbonate-converted formate formation efficiency was conducted. As a result, the TON of the catalyst was 99000, and the potassium hydrogen carbonate-converted formate formation efficiency was 0.85.

(Formate Protonation Reaction)

14 g of potassium hydroxide dissolved in 500 mL of water was charged into a base tank. 210.3 g of potassium formate that was dissolved in 180 mL of water then diluted and adjusted with water by further charging 320 mL of water, was charged into a salt tank. 500 mL of ion-exchanged water was charged into an acid tank. When the electrodialyzer was started, a voltage of 28 V and a current of 0.28 A were reached, and the electrical conductivity of the salt tank at that time was 230.1 S/m. As a dialysis treatment was conducted, the electrical conductivity gradually decreased, and after 140 minutes, the electrical conductivity reached 0. Thus, the dialysis treatment was ended. Furthermore, the voltage at that time was 28.0 V, and the current was 1.3 A. The amount of the solution (salt solution) in the salt tank after completion of dialysis was 280 mL, the amount of the solution (acid liquid) in the acid tank was 590 mL, and the liquid (base solution) in the base tank was 680 mL. 100 μL of the acid liquid was collected and dissolved in 500 μL of deuterated water, 300 μL of dimethyl sulfoxide was added as an internal standard, and $^1$H NMR was measured to quantitatively determine formic acid in the acid liquid after completion of dialysis. Furthermore, the formic acid recovery rate in the acid liquid was calculated, and as a result, it was found that the yield was 0.89. Furthermore, in order to perform quantification of potassium in the acid liquid after completion of dialysis, 20 mg of the acid liquid was collected and diluted to 50 times with water, the dilution was measured with a potassium ion meter, and then the (formic acid/(potassium formate+formic acid)) ratio in the acid liquid was calculated, which was found to be 0.99.

Finally, from the results of examination of the formate forming reaction and the formate protonation reaction, the potassium hydrogen carbonate-converted formic acid recovery rate was 0.76.

Example 5

(Formate Forming Reaction)

1 mL of water was weighed out and put in a glass vial equipped with a stirring rod in a glovebox under an inert gas, 5 mmol of potassium hydrogen carbonate was added thereto, and thereafter 0.12 μmol of the Ru catalyst 7 and 54 μmol of methyltrioctylammonium chloride were added to 1 mL of toluene. Thereafter, the vial was placed in an autoclave, and the autoclave was sealed and taken out of the glovebox. The autoclave was heated to 90° C. while being stirred. When the temperature reached the target temperature, the autoclave was pressurized to 4.5 MPa with hydrogen. The reaction mixture was stirred for 12 hours, thereafter the reaction mixture was cooled with an ice bath, and pressure was carefully released. An upper layer of the solution after the reaction was removed, and an aqueous solution of a lower layer containing potassium formate and unreacted potassium hydrogen carbonate remained. 100 μL of the aqueous solution of the lower layer was collected and dissolved in 500 μL of deuterated water, 300 μL of dimethyl sulfoxide was added as an internal standard, and then $^1$H NMR was measured. Thus, calculation of the TON of the catalyst and the potassium hydrogen carbonate-converted formate formation efficiency was conducted. As a result, the TON of the catalyst was 25000, and the potassium hydrogen carbonate-converted formate formation efficiency was 0.60.

(Formate Protonation Reaction)

14 g of potassium hydroxide dissolved in 500 mL of water was charged into a base tank. 210.3 g of potassium formate dissolved in 500 mL of water was charged into a salt tank. 500 mL of ion-exchanged water was charged into an acid tank. When the electrodialyzer was started, a voltage of 28 V and a current of 0.27 A were reached, and the electrical conductivity of the salt tank at that time was 230.1 S/m. As a dialysis treatment was conducted, the electrical conductivity gradually decreased, and after 140 minutes, the electrical conductivity reached 0. Thus, the dialysis treatment was ended. Furthermore, the voltage at that time was 28.0 V, and the current was 1.3 A. The amount of the solution (salt solution) in the salt tank after completion of dialysis was 280 mL, the amount of the solution (acid liquid) in the acid tank was 590 mL, and the liquid (base solution) in the base tank was 680 mL. 100 μL of the acid liquid was collected and dissolved in 500 μL of deuterated water, 300 μL of dimethyl sulfoxide was added as an internal standard, and $^1$H NMR was measured to quantitatively determine formic acid in the acid liquid after completion of dialysis. Furthermore, the formic acid recovery rate in the acid liquid was calculated, and as a result, it was found that the yield was 0.90. Furthermore, in order to perform quantification of potassium in the acid liquid after completion of dialysis, 20 mg of the acid liquid was collected and diluted to 50 times with water, the dilution was measured with a potassium ion meter, and then the (formic acid/(potassium formate+formic acid)) ratio in the acid liquid was calculated, which was found to be 0.98.

Finally, from the results of examination of the formate forming reaction and the formate protonation reaction, the potassium hydrogen carbonate-converted formic acid recovery rate was 0.54.

Example 6

(Formate Forming Reaction)

1 mL of water was weighed out and put in a glass vial equipped with a stirring rod in a glovebox under an inert gas, 10 mmol of potassium hydrogen carbonate was added thereto, and thereafter 0.12 μmol of the Ru catalyst 7 and 54 μmol of methyltrioctylammonium chloride were added to 1 mL of toluene. Thereafter, the vial was placed in an autoclave, and the autoclave was sealed and taken out of the glovebox. The autoclave was heated to 90° C. while being stirred. When the temperature reached the target temperature, the autoclave was pressurized to 4.5 MPa with hydrogen. The reaction mixture was stirred for 18 hours, thereafter the reaction mixture was cooled with an ice bath, and pressure was carefully released. An upper layer of the solution after the reaction was removed, and an aqueous solution of a lower layer containing potassium formate and unreacted potassium hydrogen carbonate remained. 100 μL of the aqueous solution of the lower layer was collected and dissolved in 500 μL of deuterated water, 300 μL of dimethyl sulfoxide was added as an internal standard, and then $^1$H NMR was measured. Thus, calculation of the TON of the catalyst and the potassium hydrogen carbonate-converted formate formation efficiency was conducted. As a result, the TON of the catalyst was 56000, and the potassium hydrogen carbonate-converted formate formation efficiency was 0.68.

(Formate Protonation Reaction)

14 g of potassium hydroxide dissolved in 500 mL of water was charged into a base tank. 210.3 g of potassium formate that was dissolved in 250 mL of water then diluted and adjusted with a two-fold amount of water by further charging 250 mL of water, was charged into a salt tank. When the electrodialyzer was started, a voltage of 28 V and a current of 0.27 A were reached, and the electrical conductivity of the salt tank at that time was 230.1 S/m. As a dialysis treatment was conducted, the electrical conductivity gradually decreased, and after 140 minutes, the electrical conductivity reached 0. Thus, the dialysis treatment was ended. Furthermore, the voltage at that time was 28.0 V, and the current was 1.30 A. The amount of the solution (salt solution) in the salt tank after completion of dialysis was 280 mL, the amount of the solution (acid liquid) in the acid tank was 590 mL, and the liquid (base solution) in the base tank was 680 mL. 100 μL of the acid liquid was collected and dissolved in 500 μL of deuterated water, 300 μL of dimethyl sulfoxide was added as an internal standard, and $^1$H NMR was measured to quantitatively determine formic acid in the acid liquid after completion of dialysis. Furthermore, the formic acid recovery rate in the acid liquid was calculated, and as a result, it was found that the yield was 0.88. Furthermore, in order to perform quantification of potassium in the acid liquid after completion of dialysis, 20 mg of the acid liquid was collected and diluted to 50 times with water, the dilution was measured with a potassium ion meter, and then the ratio (formic acid/(potassium formate+formic acid)) in the acid liquid was calculated, which was found to be 0.98.

Finally, from the results of examination of the formate forming reaction and the formate protonation reaction, the potassium hydrogen carbonate-converted formic acid recovery rate was 0.60.

Comparative Example 1

(Formate Forming Reaction)

1 mL of water was weighed out and put in a glass vial equipped with a stirring rod in a glovebox under an inert gas, 1 mmol of potassium hydrogen carbonate was added thereto, and thereafter 0.12 μmol of the Ru catalyst 1 and 54 μmol of methyltrioctylammonium chloride were added to 1 mL of toluene. Thereafter, the vial was placed in an autoclave, and the autoclave was sealed and taken out of the glovebox. The autoclave was heated to 90° C. while being stirred. When the temperature reached the target temperature, the autoclave was pressurized to 4.5 MPa with hydrogen. The reaction mixture was stirred for 2.5 hours, thereafter the reaction mixture was cooled with an ice bath, and pressure was carefully released. An upper layer of the solution after the reaction was removed, and an aqueous solution of a lower layer containing potassium formate and unreacted potassium hydrogen carbonate remained. 100 μL of the aqueous solution of the lower layer was collected and dissolved in 500 μL of deuterated water, 300 μL of dimethyl sulfoxide was added as an internal standard, and then $^1$H NMR was measured. Thus, calculation of the TON of the catalyst and the potassium hydrogen carbonate-converted formate formation efficiency was conducted. As a result, the TON of the catalyst was 5600, and the potassium hydrogen carbonate-converted formate formation efficiency was 0.67.

(Formate Protonation Reaction)

14 g of potassium hydroxide dissolved in 500 mL of water was charged into a base tank. 42.06 g of potassium formate dissolved in 500 mL of water was charged into a salt tank. 500 mL of ion-exchanged water was charged into an acid tank. When the electrodialyzer was started, a voltage of 28 V and a current of 0.16 A were reached, and the electrical conductivity of the salt tank at that time was 74.8 S/m. As a dialysis treatment was conducted, the electrical conductivity gradually decreased, and after 46 minutes, the electrical conductivity reached 0. Thus, the dialysis treatment was ended. Furthermore, the voltage at that time was 28.0 V, and the current was 0.78 A. The amount of the solution (salt solution) in the salt tank after completion of dialysis was 425 mL, the amount of the solution (acid liquid) in the acid tank was 510 mL, and the liquid (base solution) in the base tank was 547 mL. 100 μL of the acid liquid was collected and dissolved in 500 μL of deuterated water, 300 μL of dimethyl sulfoxide was added as an internal standard, and $^1$H NMR was measured to quantitatively determine formic acid in the acid liquid after completion of dialysis. Furthermore, the formic acid recovery rate in the acid liquid was calculated, and as a result, it was found that the yield was 0.86. Furthermore, in order to perform quantification of potassium in the acid liquid after completion of dialysis, 22 mg of the acid liquid was collected and diluted to 55 times with water, the dilution was measured with a potassium ion meter, and then the ratio (formic acid/(potassium formate+formic acid)) in the acid liquid was calculated, which was found to be 0.98.

Finally, from the results of examination of the formate forming reaction and the formate protonation reaction, the potassium hydrogen carbonate-converted formic acid recovery rate was 0.58.

<Method for Quantifying Potassium Formate or Formic Acid in Solution>

100 μL of a sample solution was collected and dissolved in 500 μL of deuterated water, 300 μL of dimethyl sulfoxide was added as an internal standard, and then $^1$H NMR measurement was conducted. The molar amount X (mol) of potassium formate or formic acid included in the solution (molar amount (mol) of potassium formate or formic acid formed by a reaction) was calculated by the following formula.

$$X=(W/M)\times(Ia\times Ib/R)\times(A/B) \quad \text{formula 2}$$

(In the formula 2, W represents the amount (g) of dimethyl sulfoxide used for quantification of potassium formate, M represents the molecular weight of dimethyl sulfoxide, R represents the ratio of the number of protons of dimethyl sulfoxide to the number of protons of potassium formate, Ia represents the proton NMR integration value of potassium formate, Ib represents the proton NMR Integration value of dimethyl sulfoxide, A represents the mass (g) of an aqueous solution in a lower layer obtained by the following reaction, and B represents the mass (g) of an aqueous solution used for quantification of potassium formate.)

Here, since W is 0.33, M is 78.13, and R is 6, formula 2 is as follows.

$$X=0.0007\times Ia\times Ib\times(A/B)$$

<Calculation of Turnover Number (TON) of Catalyst>

The calculation of the "TON of catalyst" described in Table 1 was determined by dividing the molar amount (mol) of potassium formate formed in the reaction by 0.00012 (mol), which is the molar amount of the catalyst used in the reaction.

<Method for Calculating Potassium Hydrogen Carbonate-Converted Formate Formation Efficiency>

The calculation of the potassium hydrogen carbonate-converted formate formation efficiency was determined by dividing the molar amount (mol) of potassium formate formed in the reaction by the molar amount (mol) of the amount of potassium hydrogen carbonate used in the reaction.

<Method for Calculating Purity of Formic Acid in Acid Liquid>

In order to conduct quantification (mol) of potassium ions in the solution of the acid tank (acid liquid) after completion of dialysis, a compact potassium ion meter LAQUAtwin <K-11> manufactured by HORIBA, Ltd. was used. The purity of formic acid in the acid liquid (ratio (formic acid/(potassium formate+formic acid)) in the acid solution) was calculated by dividing the value obtained by subtracting the amount of potassium ions (mol) from the amount (mol) of potassium formate or formic acid present in the acid liquid, by the amount (mol) of potassium formate and formic acid present in the acid liquid.

<Method for Calculating Formic Acid Recovery Rate in Acid Liquid>

Calculation of the formic acid recovery rate in the acid liquid for the formate protonation reaction was determined by dividing the molar amount (mol) of formic acid present in the acid liquid after the dialysis treatment by the molar amount (mol) of potassium formate in the solution (salt liquid) charged into the salt tank.

<Method for Calculating Potassium Hydrogen Carbonate-Converted Formic Acid Recovery Rate>

The efficiency assumed to be recoverable as formic acid from potassium hydrogen carbonate through the steps from the formate forming reaction to the formate protonation reaction was determined by multiplying the potassium hydrogen carbonate-converted formate formation efficiency by the formic acid recovery rate in the acid liquid in the formate protonation reaction.

The obtained results were determined by the following determination criteria.

A: When the TON of the catalyst is 50,000 or more, and the potassium hydrogen carbonate-converted formic acid recovery rate is 0.6 or more, B: when the TON of the catalyst is 20,000 or more and less than 50,000, and the potassium hydrogen carbonate-converted formic acid recovery rate is 0.5 or more and less than 0.6, C: when the TON of the catalyst is 10,000 or more and less than 20,000, and the potassium hydrogen carbonate-converted formic acid recovery rate is 0.5 or more and less than 0.6, D: when the TON of the catalyst is less than 10,000

The above Examples and Comparative Examples are described in Table 1.

TABLE 1

| | | Example 1 | Example 2 | Example 3 | Example 4 | Example 5 | Example 6 | Comparative Example 1 |
|---|---|---|---|---|---|---|---|---|
| Formate forming reaction | Catalyst used | Ru catalyst 1 | | | | Ru catalyst 7 | | Ru catalyst 1 |
| | Potassium hydrogen carbonate concentration (mol/L) | 2.5 | 5 | 10 | 14 | 5 | 10 | 1 |
| | Reaction time (hr) | 2.5 | 2.5 | 2.5 | 2.5 | 12 | 18 | 2.5 |
| | TON of catalyst | 13,000 | 27,500 | 65,000 | 99,000 | 25,000 | 56,000 | 5,600 |
| | Potassium hydrogen carbonate-converted formate formation efficiency | 0.64 | 0.66 | 0.78 | 0.85 | 0.60 | 0.68 | 0.67 |
| Adjustment of formate solution | Solution concentration step | Not required | | | | | | |
| | Dilution step | — | — | Yes | Yes | — | Yes | — |
| Formate protonation reaction | Potassium formate concentration in salt liquid (mol/L) | 2.5 | 5 | 5 | 5 | 5 | 5 | 1 |
| | Ratio (Formic acid/(potassium formate + formic acid)) in acid liquid | 0.98 | 0.99 | 0.99 | 0.99 | 0.98 | 0.98 | 0.98 |
| | Formic acid recovery rate in acid liquid | 0.85 | 0.90 | 0.89 | 0.89 | 0.90 | 0.88 | 0.86 |
| Potassium hydrogen carbonate-converted formic acid recovery rate | | 0.54 | 0.59 | 0.69 | 0.76 | 0.54 | 0.60 | 0.58 |
| Determination | | C | B | A | A | B | A | D |

It could be confirmed that Examples 1 to 6 in which a formate forming reaction was carried out using the method for producing a formate of the invention, showed high TON (Turnover Number) under the respective reaction conditions, also had high potassium hydrogen carbonate-converted formate formation efficiency, and can produce a formate in high yield and with excellent productivity.

Furthermore, it could be confirmed that Examples 1 to 6 in which formic acid was produced using the method for producing formic acid of the invention, showed high TON (Turnover Number) under the respective reaction conditions and can produce formic acid in high yield and with excellent productivity.

The TONs determined by the TON calculation method specified above for the Ru catalyst 1 and Ru catalyst 7 used in the present Examples were 66,000 and 56,000, respectively.

Examples and Comparative Examples in which an antifreezing effect of the formate obtained in the invention was verified, are described below.

Example 7

A formate forming reaction was conducted according to the method described in Example 3, by adjusting the reaction scale to be ten times (using 10 mL of water). For the aqueous solution of the lower layer after the reaction, water was evaporated by using an evaporator, and then the residue was further dried by using an oven at 60° C. to obtain a white powder.

Example 8

A formate forming reaction was conducted according to the method described in Example 3, by adjusting the reaction scale to be ten times (using 10 mL of water). 1.0 g of formic acid (manufactured by FUJIFILM Wako Pure Chemical Corporation, product No. 063-05895) was added to the aqueous solution of the lower layer after the reaction. Water was evaporated by using an evaporator, and then the residue was further dried by using an oven at 60° C. to obtain a white powder.

Example 9

A formate forming reaction was conducted according to the method described in Example 3, by adjusting the reaction scale to be ten times (using 10 mL of water). 1.3 g of acetic acid (manufactured by FUJIFILM Wako Pure Chemical Corporation, product No. 017-00256) was added to the aqueous solution of the lower layer after the reaction. Water was evaporated by using an evaporator, and then the residue was further dried by using an oven at 60° C. to obtain a white powder.

(Method for Evaluating Antifreezing Performance)

6 to 7 g of ice was placed on Petri dishes, and 0.5 g each of the white powders obtained in Examples 7 to 9 as well as calcium chloride (manufactured by FUJIFILM Wako Pure Chemical Corporation, product No. 038-24985) (Comparative Example 2) and urea (manufactured by FUJIFILM Wako Pure Chemical Corporation, product No. 213-00173)

(Comparative Example 3) as comparisons were sprinkled on the ice. The Petri dishes were placed in a constant temperature chamber at −5° C., the amount of melted ice was measured after one hour, and the proportion of the amount with respect to the initial ice weight was designated as ice melting rate. The amount of melted ice was determined by causing tissue paper to soak the water and calculating an increment in weight.

The obtained results are shown in the following Table 2.

TABLE 2

| | Ice melting rate (%) | Remarks |
|---|---|---|
| Example 7 | 42 | |
| Example 8 | 48 | Formic acid added |
| Example 9 | 55 | Acetic acid added |
| Comparative Example 2 | 47 | Calcium chloride |
| Comparative Example 3 | 36 | Urea |

It was clearly found that the formate produced in the invention has higher ice melting performance than urea, which is a representative example of a non-chloride-based antifreezing agent, and the performance is improved by neutralizing the carbonate or hydrogen carbonate remaining after the formate production process with an acid.

INDUSTRIAL APPLICABILITY

According to the invention, a method for producing a formate, in which a formate as a precursor of formic acid can be produced in high yield and with excellent productivity, a method for producing formic acid, and a method for producing an antifreezing agent can be provided.

The invention was described in detail and with reference to specific embodiments. However, it is obvious to those ordinarily skilled in the art that various modifications and alterations can be made without departing from the spirit and scope of the invention.

REFERENCE SIGNS LIST

1, 2, 3, 5: valve
10: formate production apparatus
20: diluting apparatus
30: electrodialyzer
40: diluting water storage unit
50: hydrogen cylinder
60: carbon dioxide cylinder
70: water supply unit
80: formic acid supply unit
100: formic acid production system
L1, L2: pipe
L3, L4, L5, L6, L7, L9: flow channel

The invention claimed is:

1. A method for producing a formate, the method comprising:

a first step of reacting hydrogen with carbon dioxide, a hydrogen carbonate or a carbonate using a catalyst in the presence of a solvent to form the formate in a reaction liquid, wherein the reaction is a two-phase system in which an organic solvent and an aqueous solvent are present in a separated state in the solvent, wherein, in the first step, a quaternary ammonium salt is used as a phase transfer catalyst, and provided that, when the first step reacts hydrogen with a hydrogen carbonate or a carbonate, a concentration of the hydrogen carbonate or the carbonate in the reaction is 2.5 mol/L or more.

2. The method for producing a formate according to claim 1 wherein the catalyst is a metal complex catalyst, and a ligand of the metal complex catalyst is further added.

3. The method for producing a formate according to claim 1, wherein the catalyst is at least one selected from a ruthenium complex represented by the following Chemical Formula 1, a tautomer or stereoisomer thereof, and a salt compound of the complex, tautomer or stereoisomer:

Chemical Formula 1:

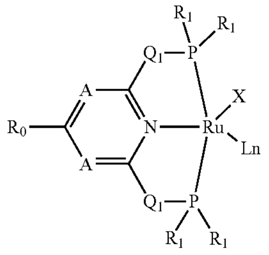

wherein, in Chemical Formula 1:

$R_0$ represents a hydrogen atom or an alkyl group, $Q_1$ each independently represents $CH_2$, NH or O, $R_1$ each independently represents an alkyl group or an aryl group, provided that when $Q_1$ represents NH or O, at least one of $R_1$ represents an aryl group, A each independently represents CH, $CR_5$ or N, wherein $R_5$ represents an alkyl group, an aryl group, an aralkyl group, an amino group, a hydroxy group or an alkoxy group, X represents a halogen atom, and in Ln, L represents a ligand and n is an integer of 0 to 3, wherein, when more than one L are present, L each independently represents a neutral or anionic ligand.

4. The method for producing a formate according to claim 3, wherein;

n is an integer of 1 to 3, and the ligand L is represented by the following Chemical Formula 4:

Chemical Formula 4:

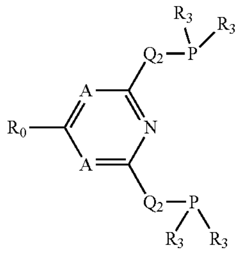

wherein, in Chemical Formula 4:

$R_0$ represents a hydrogen atom or an alkyl group, $Q_2$ each independently represents NH or O, $R_3$ each independently represents an aryl group, and A each independently represents CH, $CR_5$ or N, wherein $R_5$ represents an alkyl group, an aryl group, an aralkyl group, an amino group, a hydroxy group or an alkoxy group.

5. The method for producing a formate according to claim 1, wherein the organic phase contains toluene or dioxane.

6. A method for producing formic acid, the method comprising:

a step of producing a formate by the method according to claim 1; and a second step of protonating at least a part of the formate by electrodialysis to form formic acid and water.

7. The method for producing formic acid according to claim 6, wherein the aqueous phase is separated, a concentration of the formate in the aqueous phase is adjusted by dilution, and then the aqueous phase is used in the second step.

8. The method for producing formic acid according to claim 7, wherein the water formed in the second step is used for the dilution.

9. The method for producing formic acid according to claim 6, wherein the aqueous phase is separated, an acid is added thereto to conduct a decarbonation treatment, and then the aqueous phase is used in the second step.

10. A method for producing an antifreezing agent, the method comprising:

a step of producing a formate by the method for producing a formate according to claim 1.

11. The method for producing an antifreezing agent according to claim 10, wherein the method further includes a step of adding at least one or more acids selected from the group consisting of formic acid and acetic acid to the formate.

* * * * *